United States Patent [19]

Bicker et al.

[11] 4,332,943

[45] Jun. 1, 1982

[54] PROCESS FOR THE PREPARATION OF PYRIDINE

[75] Inventors: Richard Bicker, Frankfurt am Main; Rüdiger Erckel, Eppstein, both of Fed. Rep. of Germany

[73] Assignee: Hoechst Aktiengesellschaft, Frankfurt am Main, Fed. Rep. of Germany

[21] Appl. No.: 292,805

[22] Filed: Aug. 14, 1981

[30] Foreign Application Priority Data

Aug. 16, 1980 [DE] Fed. Rep. of Germany ....... 3031014

[51] Int. Cl.$^3$ .................. C07D 213/06; C07D 213/12
[52] U.S. Cl. .................................................. 546/253
[58] Field of Search ......................................... 546/253

[56] References Cited

U.S. PATENT DOCUMENTS 3,166,556  1/1965  Fremery et al. ..................... 546/253
3,989,706  11/1976  Ichikawa et al. .................... 546/253

FOREIGN PATENT DOCUMENTS

48/64020  9/1973  Japan ................................... 546/253

*Primary Examiner*—Robert T. Bond
*Attorney, Agent, or Firm*—Curtis, Morris & Safford

[57] ABSTRACT

Pyridine is prepared by ammoxidation (=reaction with oxygen or an oxygen-containing gas and ammonia, if appropriate in the presence of steam) of cyclopentadiene in the presence of a tellurium-free silica gel catalyst, $\gamma$-$Al_2O_3$ catalyst and/or aluminum silicate catalyst, which is preferably also doped with transition metal oxides and/or the oxides of gallium and/or indium and, if appropriate, also contains trivial quantities of further customary additives. The surface area of the catalyst should be between about 75 and 800 $m^2/g$ and the pore volume between about 0.2 and 2 $cm^3/g$, and the reaction temperature should be between about 200° and 400° C.

The pyridine formed in the process is free from picolines and higher homologs.

4 Claims, No Drawings

PROCESS FOR THE PREPARATION OF PYRIDINE

Pyridine is an important solvent and starting material or intermediate product in numerous fields, such as, for example, in the plant protection sector and pharmaceutical sector.

Various routes and processes are known for preparing and obtaining pyridine and pyridine substitution products (pyridine bases). An instructive review of the state of the art in this context in 1966 is given, for example, by the article by K.—K. Moll "Ueber die Gewinnung von Pyridin und Alkylpyridinen" [On Obtaining Pyridine and Alkyl Pyridines] in Zeitschrift Chem. Techn. 19, 528 to 537 (1967).

According to this publication, pyridine bases were previously obtained exclusively from upgraded coal products. Apart from the fact that only relatively small quantities of pyridine bases are obtainable in this manner, the separation of the pyridine bases which are in this case always contained in a mixture causes considerable difficulties; in addition, owing to their very high sulfur content throughout, the pyridine bases obtained from coal are unsuitable for many purposes.

The development of purely synthetic routes for the preparation of pyridine bases has therefore already been attempted at an early stage. In these routes, particularly aliphatic carbonyl compounds—for example, acrolein or acetaldehyde+formaldehyde—and ammonia $NH_3$ were used as starting compounds. However, the yields of pyridine bases obtained thereby are relatively low—they are between a few percent and about 20 to 30% of theory—and the proportion of unsubstituted pyridine therein is likewise low. Pure pyridine cannot be obtained in this manner.

The so-called ammozonolysis—that is to say, the joint action of ozone and ammonia—uses hydrocarbons, such as, for example, cyclopentadiene, as starting compounds. In this process, pyridine is supposed to have been obtained in a yield of 18%. However, the method is hardly suitable for taking over on an industrial scale, owing to the ozone which is unpleasant to handle.

The more recent processes for the preparation of pyridine bases also mainly use hydrocarbons as starting compounds. Thus, according to the two-step process described in GB-PS [British Patent Specification] No. 1,134,163 (published in 1968), propylene and/or butylene in the vapor phase are first catalytically oxidized using oxygen or an oxygen-containing gas at temperatures between 300° and 750° C., and the carbonyl compounds formed thereby are then condensed with ammonia at temperatures of up to 600° C. to give pyridines.

In this process, catalysts which are known for oxidations, such as, for example, $V_2O_5$, V-B-P-O complexes, Te-compounds, etc., are used as oxidation catalysts; silicic acid, $Al_2O_3$, alumosilicates, kieselguhr, alundum, boron phosphate, etc., are examples of condensation catalysts.

Using propylene as a starting compound, the yields of pyridine bases in this process are up to about 30% of theory, relative to propylene reacted, about half this yield being pyridine. (Remainder: principally picoline.) In this process as well, pure pyridine (without homologs) is not produced.

Finally, an attempt has also been made to obtain pyridine or pyridine bases directly in a single reaction step, using hydrocarbons as starting compounds. In processes of this type, the corresponding hydrocarbons are virtually simultaneously oxidized and condensed, using oxygen or an oxygen-containing gas (air), ammonia and, if appropriate, steam over suitable catalysts. The processes which proceed under such conditions have become known under the designation "ammoxidation".

Japanese preliminary published application Sho-48-64020, which appeared in 1973, of Nissan (Japan) refers to such an ammoxidation. According to this publication, N-containing compounds, particularly 1-cyano-1,3-"pentadiene" (whereby 1-cyano-1,3-butadiene is probably meant) and pyridine, are prepared by ammoxidation of $C_5$ hydrocarbons. The oxides of bismuth, vanadium, molybdenum and phosphorus are given as catalysts, the atomic ratio of the elements Bi:V:Mo:P being stated as (0–1):(0–1):(1–9):0.1. Carrier substances for the catalysts are, for example, alumina, colloidal silicic acid, etc. The carrier substances are reported to influence the yield of 1-cyano-1,3-"pentadiene" according to the following series: Active charcoal<<silica gel<<pumice<carborundum<alundum.

The conversion is reported to increase with decreasing particle size (and increasing surface area) of the catalysts.

Temperatures between 450° and 550° C. are given as the reaction temperatures.

Using the starting compound 1,3-pentadiene, the best pyridine yield is 6%, relative to 1,3-pentadiene reacted.

According to the table at the end of the preliminary published application (using the catalyst V-Mo-P oxides on an alundum carrier), no pyridine is obtained using cyclopentadiene as the hydrocarbon starting compound.

A further ammoxidation process for the preparation of pyridine bases is known from Japanese preliminary published application Sho 49-1569 of Teijin (Japan), published in 1974. Hydrocarbons used as starting compounds for this process are saturated or unsaturated hydrocarbons with at least 2 C atoms.

Catalysts are acid solids, the following materials being mentioned: acid clay minerals (bentonite, kaolin, etc.), natural and synthetic cationic zeolites (preferably charged with Na ions or with 2- to 3-valent metal ions, particularly the 3-valent ions of the rare earth metals), silica gel, silicic acid/alumina, silicic acid/MgO, silicic acid/alumina/MgO, silicic acid/zirconium oxide, sulfates (nickel sulfate, aluminum sulfate, etc.), phosphates (calcium phosphate, zinc phosphate, etc.), carbonates ($CaCO_3$, etc.) and so on. Silicic acid/alumina and zeolite are used as catalysts in the examples.

The reaction temperatures are reported to be between 200° and 800° C., preferably between 300° and 600° C.; normal pressure, but also reduced pressure and increased pressure, is given as the pressure for the process.

Starting from the hydrocarbon propylene which is preferred and which is also used in all examples, small yields of pyridine—mostly mixed with picolines—are obtained (for example in Example 1: 0.0090 parts of pyridine/h ≙ 0.0096%·of pyridine).

Cyclopentadiene is also mentioned, inter alia, amongst the hydrocarbon starting compounds suitable for the process. As our own experiments using a zeolite catalyst have shown, however, only very little pyridine is obtained by ammoxidation of cyclopentadiene.

Even if the zeolite catalyst is doped with the known oxidation catalyst $V_2O_5$, for example, only relatively little pyridine is formed by these experiments of ours.

The ammoxidation likewise of saturated or unsaturated hydrocarbons having at least 2 C atoms over an acid solid catalyst is also known from German Offenlegungsschrift No. 2,401,103 of Teijin, published in 1975. An essential characteristic of the catalyst used in this case is the content of tellurium or tellurium dioxide.

The tellurium dioxide can be applied to or mixed with acid clay minerals (bentonite, kaolin), oxides such as $SiO_2$, $Al_2O_3$, $V_2O_5$, ZnO, etc., complex oxides, such as $SiO_2.Al_2O_3$, $SiO_2.Al_2O_3.ZrO_2$, $SiO_2.MgO$, etc., sulfates (nickel sulfate, manganese sulfate, etc.), nitrates, phosphates, carbonates, halides, etc.

A preferred catalyst further contains $Sb_2O_3$ and platinum, in addition to the obligatory $TeO_2$.

The surface area of the catalysts is stated to be at least 30 $m^2/g$, preferably 50 $m^2/g$; values of up to above 600 $m^2/g$ are evident from the examples.

Temperatures between 300° and 500° C., preferably between 350° and 450° C., are given as reaction temperatures.

Starting from propylene, which is preferred as the hydrocarbon starting compound, mixtures of pyridine and of homologs thereof are obtained; the maximum pyridine yields obtained are about 14%, relative to propylene reacted, together with varying quantities of picoline. Cyclopentadiene is also mentioned amongst the hydrocarbon starting compounds suitable for the process; appropriate examples for carrying out the reaction are, however, lacking. However, according to our own experiments, no pyridine is obtained by ammoxidation of cyclopentadiene over a $TeO_2$-containing $SiO_2$ catalyst.

The article by the Italian authors L. Forni and N. Stanga in J. Catalysis 59, 148 to 154 (1979) is based on the last-mentioned German Offenlegungsschrift No. 2,401,103, the article being concerned with a closer investigation of the synthesis of pyridine bases by ammoxidation of propylene over a $TeO_2/SiO_2/Al_2O_3$ catalyst. In the article, the method which uses the $TeO_2$ catalyst is designated as the most promising of the various methods of catalytic ammoxidation of olefines. Investigations of the catalyst $TeO_2/SiO_2/Al_2O_3$, without or with other oxides (in this case: $Sb_2O_3$, NiO and $MnO_2$), are then reported. In this process, catalysts with surface areas of between about 180 and 670 $m^2/g$ and pore volumes of about 0.1 and 1.15 $cm^3/g$ were used and measurements of the pore radii, the acid surface centers, etc., were also carried out. As a result of the investigations, it was found that the $TeO_2$-containing $SiO_2/Al_2O_3$ catalyst is so well suited for the ammoxidation of olefines because it is said to contain, in an optimum manner, oxidizing as well as acid centers. At the oxidizing centers (based on $TeO_2$, preferably further activated by $Sb_2O_3$), the hydrocarbon starting compounds are oxidized to the corresponding carbonyl compounds (probably aldehydes), which are then condensed or cyclized with ammonia at the acid centers (based on $SiO_2/Al_2O_3$) to give the corresponding pyridine bases.

In spite of several advantages, the relatively low yield and the likewise relatively low selectivity (mixture of pyridine bases which are separable with difficulty are almost always formed) are disadvantageous for the known syntheses of pyridine bases. Owing to the increasing importance of (unsubstituted) pyridine as a solvent and for synthetic purposes, and because of the increasing demand for pyridine arising therefrom, the problem arose of developing a new pyridine synthesis or of improving the known processes in such a manner that pyridine is formed in higher yield and selectivity (as far as possible without homologs which are difficult to separate off).

This problem could be solved according to the invention by ammoxidation of cyclopentadiene over a particular—tellurium-free—catalyst at a relatively low reaction temperature (compared with the known processes).

The subject of the invention is thus a process for the preparation of pyridine by ammoxidation at elevated temperatures of a $C_5$ hydrocarbon using a catalyst based on $SiO_2$ and/or $Al_2O_3$ with a large surface area and a large pore volume, wherein (a) cyclopentadiene is used as the $C_5$ hydrocarbon, and (b) silica gel, $\gamma$-$Al_2O_3$ and/or an alumosilicate in tellurium-free form, if appropriate doped with oxides of transition metals, and/or of gallium and/or indium with surface areas of from about 75 to 800 $m^2/g$ and pore volumes of from about 0.2 to 2.0 $cm^3/g$ are used as the catalyst based on $SiO_2$ and/or $Al_2O_3$, and (c) the ammoxidation is carried out at temperatures of from about 200° to 400° C., preferably from about 250° to 350° C.

The process gives selectivities equivalent to pyridine yields of up to about 45%, relative to cyclopentadiene reacted, but no pyridine homologs which are difficult to separate off from pyridine.

It was extraordinarily surprising that, by means of the combination, according to the invention, of elements which are in themselves known in the ammoxidation of olefines, which is in itself known, a result which was very considerably improved in comparison to the known olefine ammoxidation was obtained, because, on the basis of the table at the end of Japanese preliminary published application No. Sho 48-64020 and our own attempts at re-working the process of Japanese preliminary published application No. Sho 49-1569 and German Offenlegungsschrift No. 2,401,103 using the types of catalyst given there and cyclopentadiene as the olefine starting compound, it was not to be expected that a useful—not to mention progressive—result could be achieved at all in this direction.

It was not to be expected, particularly with respect to the statement in J. Catalysis 59, 148 to 154 (1979) on the decisive significance of $TeO_2$ and its substantial importance for an optimum progress of the ammoxidation, that an even better pyridine yield and pyridine selectivity would be obtained with a tellurium-free catalyst.

Pure oxygen as well as an oxygen-containing gas can be employed as the oxidizing agent for the ammoxidation according to the invention. The use of air is preferred. The molar ratio between oxygen and the cyclopentadiene in the starting mixture fed into the reaction space is advantageously in the range of between about 0.5 and 75:1, a ratio in the range of about 1 to 20:1 being preferred.

The molar ratio between ammonia and the olefine in the starting mixture can also vary within wide limits. The molar ratio is advantageously about 0.5 to 50:1, preferably about 10 to 30:1.

Steam is not absolutely necessary as the diluent in the process according to the invention; its presence is, however, advantageous. If the reaction is carried out in the presence of steam, the molar ratio of steam to cyclopentadiene in the starting mixture should be approximately in the range of 10 to 100:1, preferably of about 15 to 65:1.

The catalysts for the process according to the invention are silica gel, γ-$Al_2O_3$ and/or aluminum silicate(s) in tellurium-free form. The catalysts can be used as they are or optionally—and preferably—in a form doped with oxides of transition metals. $V_2O_5$ is the preferred transition metal oxide for this purpose. Also the oxides of the non-transition metals gallium and indium reveal a catalytic effect. The quantity of this doping agent can be between about 0.1 and 40% by weight, relative to the total catalyst; quantities of about 0.5 to 10% by weight of doping agent are preferred.

In addition to the doping agents, the catalysts can also contain other customary additives, such as alkali metal oxides, alkali metal sulfates, alkaline earth metal oxides and noble metals of the platinum group—particularly platinum itself. The quantity of the non-noble metal additives can be of the same order of magnitude as the quantity of doping agent; the noble metal quantities are smaller: they are advantageously between only about 0.05 and 3%, preferably between only about 0.1 and 1.0%.

The catalysts which are optionally doped and also optionally provided with other customary additives should have surface areas of between about 75 and 800 $m^2/g$ (determined according to the Brunauer-Emmet-Teller=BET method) and pore volumes of between about 0.2 and 2.0 $cm^3/g$.

Examples of catalysts are listed in the following table:

preferably at about 350° to 450° C., and the metal salts are thus converted to the oxide.

Nitrates, chlorides, oxalates, acetates, tartrates and acetylacetonates, dissolved in water or alcohol or even in other solvents, such as, for example, methylene chloride, toluene, dimethylformamide, etc., are preferably used as the metal salts to be employed.

It is also possible to reduce the prepared catalyst before use, whereby ammonia, olefine, hydrogen or hydrazinehydrate, for example, can be used as the reducing agent.

If, during the course of the ammoxidation reaction according to the invention, polymer deposits form on the catalyst, a regeneration or reactivation of the catalyst by means of a treatment with air at about 300° to 500° C. can be effected. In this process, the polymer deposits are burnt off.

The reaction is carried out at a temperature in the range of about 200° to 400° C., the preferred temperature range being between about 250° and 350° C.

The reaction is preferably carried out at about atmospheric pressure or slightly elevated pressure.

The apparent time of contact is not critical. Apparent times of contact in the range from about 0.1 to about 10 seconds can be used. However, a time of contact in the range from about 0.1 to about 5 seconds is, in general, preferred.

For carrying out the process according to the invention, any apparatus can be employed which is used for carrying out oxidation reactions in the vapor phase. The process can be carried out either continuously or dis-

| Catalyst | Transition Metal Oxide | Further Additives | BET-Surface Area | Pore Volumes |
|---|---|---|---|---|
| silica gel + | 5.5% $V_2O_5$ | | 302 $m^2/g$ | 0.567 $cm^3/g$ |
| " | " | | 570 $m^2/g$ | 0.36 $cm^3/g$ |
| " | 10% $V_2O_5$ | + 10% $K_2SO_4$ | 682 $m^2/g$ | 0.667 $cm^3/g$ |
| " | 12.5% $V_2O_5$ | + 12.5% $K_2SO_4$ | 158 $m^2/g$ | 0.191 $cm^3/g$ |
| " | 12.6% $V_2O_5$ | + 0.8% $P_2O_5$ | 173 $m^2/g$ | 0.344 $cm^3/g$ |
| " | 10% $V_2O_5$ | + 10% $K_2SO_4$ | 226 $m^2/g$ | 0.424 $cm^3/g$ |
| " | 10% $V_2O_5$ | + 30% $K_2SO_4$ | 149 $m^2/g$ | 0.343 $cm^3/g$ |
| " | — | + 5.6% $In_2O_3$ | 283 $m^2/g$ | 0.523 $cm^3/g$ |
| " | — | + 3.1% $SnO_2$ | 283 $m^2/g$ | 0.532 $cm^3/g$ |
| " | 1.6% ZnO | | 283 $m^2/g$ | 0.523 $cm^3/g$ |
| " | 11.0% $V_2O_5$ | + 1.1% $Rb_2O$ | 283 $m^2/g$ | 0.523 $cm^3/g$ |
| " | 2.3% $V_2O_5$ | | 283 $m^2/g$ | 0.523 $cm^3/g$ |
| " | 2.0% $V_2O_5$ | | 680 $m^2/g$ | 0.45 $cm^3/g$ |
| " | 10%/2% $MnO_2$ | + 1% $K_2SO_4$ | 283 $m^2/g$ | 0.523 $cm^3/g$ |
| silica gel/ 0.6%/γ-$Al_2O_3$ | 7.7% $V_2O_5$ | 7.7% $K_2SO_4$ | 265 $m^2/g$ | 0.538 $cm^3/g$ |
| γ-$Al_2O_3$ | 10% $V_2O_5$ | | 78 $m^2/g$ | 0.33 $cm^3/g$ |
| " | 8.9% $V_2O_5$ | | 250 $m^2/g$ | 0.55 $cm^3/g$ |
| " | 12.8% $V_2O_5$ | | 100 $m^2/g$ | 0.55 $cm^3/g$ |
| " | 10%/1% $MoO_3$ | | 78 $m^2/g$ | 0.33 $cm^3/g$ |
| " | 10%/1% $Fe_2O_3$ | | 78 $m^2/g$ | 0.33 $cm^3/g$ |
| " | 10% | 1% $SnO_2$ | 78 $m^2/g$ | 0.33 $cm^3/g$ |
| " | 10%/1% ZnO | | 78 $m^2/g$ | 0.33 $cm^3/g$ |
| " | 5% | 0.5% $P_2O_5$ | 100 $m^2/g$ | 0.55 $cm^3/g$ |
| " | 10%/1% $TiO_2$ | | 250 $m^2/g$ | 0.55 $cm^3/g$ |
| " | 20% $V_2O_5$ | 2% $K_2TiF_6$ | 300 $m^2/g$ | 0.47 $cm^3/g$ |
| Al silicate (74.5% $SiO_2$ + 25% $Al_2O_3$) | 10% $V_2O_5$ | 10% $K_2SO_4$ | 100 $m^2/g$ | 0.28 $cm^3/g$ |
| Al silicate (86.5% $SiO_2$ + 13% $Al_2O_3$) | 10% $V_2O_5$ | 10% $K_2SO_4$ | 375 $m^2/g$ | 0.4 $cm^3/g$ |

The preparation of the catalysts can be effected according to any of the known processes for the preparation of catalysts. An example of a manner of preparation consists in impregnating previously prepared silica gel, γ-$Al_2O_3$ and/or aluminum silicate with an appropriate metal salt solution. After drying, the impregnated catalyst is calcined in a stream of air at about 200° to 600° C., continuously, it being possible to carry out the reaction in a fixed bed or in a fluid bed arrangement.

It is advisable to pre-heat the starting gas mixture.

The catalyst bed can be a fixed bed, using large catalyst particles, such as irregular molded forms, extruded forms, spheres, pellets or tablets; however, it can also be carried with a catalyst arranged in a fluid bed.

The gas stream leaving the reactor essentially contains pyridine, carbon oxides, acetonitrile and hydrocyanic acid. These reaction products can be separated from the gas stream according to processes which are in themselves known. One of these processes consists, for example, in washing the gas leaving the reactor with cold water, the pyridine and acetonitrile essentially being removed from the gas stream. The water can also be acidified for better absorption of the pyridine, in this case the unreacted ammonia also being simultaneously neutralized, and the formation of ammonium carbonate from unreacted ammonia and carbon dioxide being avoided.

The hydrocyanic acid formed likewise remains in the washing water. The gas stream which leaves the water washes essentially contains unreacted olefine, carbon dioxide, nitrogen and oxygen, and, in the case of relatively low conversion, can be again fed to the reactor after separating off the carbon dioxide, or, in the case of largely complete conversion, is discarded.

The final recovery of the pyridine takes place according to generally customary methods.

The unreacted olefine can also be removed from the gas stream which leaves the water washes by means of extraction with a non-polar solvent, such as, for example, methylene chloride, and thus be recovered.

The invention enables—starting from a simple and relatively accessible starting material (cyclopentadiene)—the preparation of pyridine in selectivities of up to about 45% of theory, and—a fact to be particularly emphasized—without picoline and other homologous pyridine bases being concomitantly formed in the process. The difficult separation of the pyridine from a mixture of pyridine bases, which is otherwise necessary (in the case of most known procedures), is thus omitted in this case. The invention therefore represents considerable progress in this field, since, in the case of the comparable known processes, the pyridine yields and pyridine selectivities are, in part, considerably lower.

A detailed description of the process according to the invention and the preparation of the catalyst is effected in association with the exemplary embodiments. The yields, conversions and selectivities given in the examples are defined as follows:

$$\text{yield:} \frac{\text{quantity of pyridine formed}}{\text{maximum quantity of pyridine expected}} \cdot 100$$

$$\text{conversion:} \frac{\text{quantity of cyclopentadiene employed} - \text{quantity of cyclopentadiene recovered}}{\text{quantity of cyclopentadiene employed}} \cdot 100$$

$$\text{selectivity:} \frac{\text{yield}}{\text{conversion}} \cdot 100$$

The reactor employed in Examples 1 to 9 was a standard reactor of stainless steel with a diameter of 2 cm. The reactor has an internal axial tube as a core for temperature measurement, in which the temperature in the catalyst load can be measured at several points with a thermoelement. The reactor tube is heated by means of a salt melt. The gases were measured into the reactor by means of rotameters, the $H_2O$ metering was effected with a hose pump and the cyclopentadiene was conveyed into the reactor from a cool wash bottle by means of a stream of nitrogen.

The product gases leaving the reactor are led through a system of traps and wash bottles and are finally analyzed by gas chromatography.

The catalysts employed in the following examples in the fixed-bed reactor were prepared according to the impregnation method.

A few comparison examples (B) follow the examples of the invention (A), the former examples showing that the ammoxidation of cyclopentadiene over various catalysts of the state of the art yields no pyridine or only very little pyridine.

(A) EXAMPLES OF THE INVENTION

Example 1

A catalyst with the composition of 10% by weight of $V_2O_5$, 30% by weight of $K_2SO_4$ on silica gel B (BET surface area: 283 $m^2/g$, pore volume 0.523 $cm^3/g$) was prepared as follows:

120 g of silica gel B were impregnated four times with a solution of 25.8 g of $NH_4VO_3$, 51.6 g of oxalic acid and 60 g of $K_2SO_4$ in 400 ml of $H_2O$. After each impregnation step the material is dried for 16 hours at 110° C.

The activation is effected by calcination of the material for 6 hours at 400° C. in a stream of air (8 l/h of air). The average particle size of the catalyst was 2–3 mm.

46 g of the above catalyst were introduced into the reactor, and 2.6 g/h of cyclopentadiene, 10 l/h of $NH_3$, 17.5 l/h of air, 18 g/h of $H_2O$ and 6 l/h of $N_2$ were conducted through the reactor at 300° C. Experiment time: 4 h.

Yield of pyridine: 12.5%; conversion: 100%; selectivity: 12.5%.

Example 2

The catalyst employed corresponds to that in Example 1. 50.3 g of this catalyst are introduced into the reactor, and 2.6 g/h of cyclopentadiene, 10 l/h of $NH_3$, 17.5 l/h of air, 18 g/h of $H_2O$ and 6 l/h of $N_2$ are conducted through the reactor at 300° C.

The catalyst is regenerated with 6 l/h of air after every half hour of running time, the system of traps at the reactor exit being disconnected. The service life of the catalyst is substantially prolonged by means of this procedure.

Yield of pyridine: 11.7%; conversion: 94.1%; selectivity: 12.5%.

Example 3

A catalyst with approximately 5.5% of $V_2O_5$ on silica gel A (BET surface area: 560 $m^2/g$; pore volume: 0.29 $cm^3/g$) was prepared as follows:

60 g of silica gel A are impregnated with a solution of 12.9 g of $NH_4VO_3$ and 25.8 g of oxalic acid in 60 ml of $H_2O$.

From the quantity of solution absorbed, a content of 5.5% of $V_2O_5$ in the prepared catalyst is calculated.

The drying and activation of the catalyst are effected as described in Example 1.

16.0 g of this catalyst are introduced into the reactor, and 0.79 g/h of cyclopentadiene, 10 g/h of $NH_3$, 18 g/h of $H_2O$ and 3.1 l/h of $N_2$ are conducted through the reactor at 300° C. Duration of experiment: 4 h. Yield of pyridine: 9.7%; conversion 67.3%; selectivity: 14.5%

Example 4

A catalyst with approximately 5.5% of $V_2O_5$ on silica gel B is prepared analogously to Example 3. 8.2 g of this catalyst are introduced into the reactor, and 0.79 g/h of cyclopentadiene, 5.0 l/h of $NH_3$, 17.5 l/h of air, 3.3 l/h $N_2$ and 18 g/h of $H_2O$ are conducted through the reactor at 300° C. Duration of experiment: 4 h.

Yield of pyridine: 8.2%, conversion: 66.4%; selectivity: 12.3%.

Example 5

A 50% strength hydrazinehydrate solution is added to the catalyst from Example 4 and the latter is dried in a stream of $N_2$.

10.3 g of this catalyst are introduced into the reactor and 0.7 g/h of cyclopentadiene, 5.0 l/h of $NH_3$, 17.5 l/h of air, 3.3 l/h of $N_2$ and 18 g/h of $H_2O$ are conducted through the reactor at 300° C. Duration of experiment: 4 h.

Yield of pyridine: 13.0%; conversion: 75.2%; selectivity: 17.3%.

Example 6

A catalyst with 1.57% of $V_2O_5$ of silica gel E was prepared as follows:

49 g of silica gel E are impregnated twice with a solution of 1.29 g of $NH_4VO_3$ and 2.58 g of oxalic acid in 50 ml of $H_2O$. Drying and activation of the material are analogous to Example 1.

15 g of this catalyst are introduced into the reactor, and 0.6 g/h of cyclopentadiene, 5.0 l/h of $NH_3$, 17.5 l/h of air, 18 g/h of $H_2O$ and 3.0 l/h of $N_2$ are conducted through the reactor at 300° C. Duration of experiment: 4 h.

Yield of pyridine: 20.6%; conversion: 71.9%; selectivity: 28.7%

Example 7

A catalyst with 1.6% of ZnO on silica gel B was prepared as follows: 47.5 g of silica gel B were impregnated twice with a solution of 2.61 g of zinc nitrate $(Zn(NO_3)_2.4H_2O)$ in 80 ml of $H_2O$. Drying and calcination were carried out as described in Example 1.

8.8 g of this catalyst were introduced into the reactor, and 0.7 g/h of cyclopentadiene, 5.0 l/h of $NH_3$, 17.5 l/h of air, 18 g/h of $H_2O$ and 3.2 l/h $N_2$ were conducted through the reactor at 300° C. Duration of experiment: 4 h.

Yield of pyridine: 3.1%; conversion: 42.4%; selectivity: 7.3%.

Example 8

A catalyst with 2.6% of $V_2O_5$ and 0.1% of Pt on silica gel B was prepared as follows:

475 g of silica gel B were impregnated twice with a solution of 23.5 g of $NH_4VO_3$ and 47.0 g of oxalic acid in 700 ml of $H_2O$.

Drying and calcination of the material are analogous to Example 1. This yields a catalyst with approximately 2.6% of $V_2O_5$ on silica gel B. 50 g of this catalyst are impregnated with a solution of 66.6 mg of $PtCl_2$ in 50 ml of 5 N HCl. Drying and calcination of the material are analogous to Example 1.

9.0 g of this catalyst are introduced into the reactor and 0.6 g/h of cyclopentadiene, 5.0 l/h of $NH_3$, 17.5 l/h of air, 18 g/h of $H_2O$ and 3.0 l/h of $N_2$ are conducted through the reactor at 300° C. Duration of experiment: 4 h.

Yield of pyridine: 11.4%; conversion 59.1%; selectivity: 19.3%

The following result is obtained without platinum, that is to say, using the previous catalyst with 2.6% of $V_2O_5$ on silica gel B:

Yield of pyridine: 8.5%; conversion 70.0%; selectivity: 12.1%

Example 9

A catalyst with the composition of 2.3% of $V_2O_5$ on silica gel B (BET surface area: 283 m$^2$/g, pore volume: 0.523 cm$^3$/g) was prepared as follows:

2.65 g of vanadylacetylacetonate were dissolved in 60 ml of methylene chloride, and 80 g of silica gel B were impregnated with this solution. The excess methylene chloride is stripped off in a rotary evaporator. The catalyst thus obtained is dried and calcined as described in Example 1.

7.17 g of the above catalyst were introduced into the reactor, and 0.6 g/h of cyclopentadiene, 5.0 l/h of $NH_3$, 17,5 l/h of air, 18 g/h of $H_2O$ and 1.1 l/h of $N_2$ were conducted through the reactor at 300° C. Experiment time: 4 h Yield of pyridine: 6.6%; conversion 47.7%; selectivity: 15.4%

Example 10

A catalyst with 20% of $V_2O_5$ on a carrier of $\gamma$-$Al_2O_3$ (BET surface area 80 m$^2$/g; pore volume 0.45 cm$^3$/g) was prepared as follows:

40 g of $\gamma$-$Al_2O_3$ spheres are impregnated twice with a solution of 12.9 g of ammoniumvanadate ($NH_4VO_3$) and 25.8 g of oxalic acid in 40 ml of $H_2O$. After each impregnation step, the material is dried for 16 hours at 110° C. The activation is effected as described in Example 1.

12.4 g of the above catalyst are introduced into the reactor, and 0.5 g/h of cyclopentadiene, 5 l/h of $NH_3$, 17.5 l/h of air, 3.0 l/h of $N_2$ and 18 g/h of $H_2O$ are conducted through the reactor at 300° C.

Duration of experiment: 4 h.

Yield of pyridine: 5.3%; conversion 98.8%; selectivity: 5.4%.

Example 11

Undoped silica gel E (BET surface area: 667 m$^2$/g, pore volume: 0.31 cm$^3$/g) is employed as a catalyst. The gel is treated with water, whereupon the silica gel spheres, which have diameters of 3–5 mm, crack under great development of heat and finally have diameters of about 1 mm. The gel is then dried for 8 hours at 150° C., and is employed in this form.

49.9 g of the above gel are introduced into the reactor, and 0.4 g/h of cyclopentadiene, 5.0 l/h of $NH_3$, 17.5 l/h of air, 18 g/h of $H_2O$ and 0.5 l/h of $N_2$ are conducted through the reactor at 300° C.

Experiment time: 4 h.

Yield of pyridine: 20.6%; conversion 98.4%; selectivity: 20.8%.

Example 12

16.9 g of the catalyst described in Example 6 are introduced into the reactor, and 0.3 g/h of cyclopentadiene, 5.0 l/h of $NH_3$, 17.5 l/h of air and 20 l/h of $N_2$ are conducted through the reactor at 300° C. Duration of experiment: 5 h Yield of pyridine: 37.0%; conversion: 82.7%; selectivity: 44.7%

(B) COMPARISON EXAMPLES

Comparison Example 1

(Use of zeolite or molecular sieve catalysts corresponding to Japanese preliminary published application Sho-49-1569):

(a) undoped molecular sieve catalyst
catalyst: molecular sieve 13 x (Union Carbide Corporation/US);

46.2 g of the molecular sieve 13 x are introduced into the reactor, and 9.4 g/h of cyclopentadiene, 10 l/h of $NH_3$, 17.5 l/h of air, 16 g/h of $H_2O$ and 11 l/h of $N_2$ are conducted through the reactor at 300° C. Experiment time: 4 h;

Yield of pyridine: 0%.

(b) molecular sieve catalyst doped with $V_2O_5$:

(b1) 7.2% of $V_2O_5$ on molecular sieve 13 x (Union Carbide): pyridine yield: 1.22%.

(b2) 5% of $V_2O_5$ on molecular sieve K 306 (Süd-Chemie) pyridine yield: 3.05%.

(b3) 5% of $V_2O_5$ on molecular sieve AW 500 (Linde): pyridine yield: 1.3%.

(b4) 10% of $V_2O_5$, 10% of $K_2SO_4$ on molecular sieve KA-120 (Süd-Chemie): pyridine yield: 2.4% selectivity: 4.6%.

Comparison Example 2

(Use of a $TeO_2$-containing $SiO_2$ catalyst corresponding to German Offenlegungsschrift No. 2,401,103). A catalyst containing tellurium dioxide and having approximately 3.2% of $TeO_2$ on silica gel B (BET surface area 283 $m^2/g$, pore volume 0.523 $cm^3/g$) was prepared as follows:

47.5 g of silica gel B are impregnated twice with a solution of 1.6 g of $TeO_2$ in 100 ml of semi-concentrated $HNO_3$ (approximately 30% by weight). After each impregnation the material is dried for 16 hours at 110° C. The calcination is effected in a stream of air at 400° C. for 6 hours. 8.1 g of the above catalyst are introduced into the reactor, and 0.9 g/h of cyclopentadiene, 5 l/h of $NH_3$, 17.5 l/h of air, 15 g/h of $H_2O$ and 3.0 l/h of $N_2$ are conducted through the reactor at 300° C. Experiment time: 4 h.

Yield of pyridine: 0%.

Comparison Example 3

(Use of a $TeO_2$-containing $SiO_2$ catalyst corresponding to German Offenlegungsschrift No. 2,401,103): A tellurium-containing catalyst with approximately 10% of $TeO_2$ on silica gel E (BET surface area: 667 $m^2/g$, pore volume: 0.523 $cm^3/g$) was prepared as follows: 45 g of silica gel E were impregnated three times with a solution of 5.5 g of $TeO_2$ in 150 ml of concentrated $HNO_3$. After each impregnation, the material is dried for 16 hours at 110° C. The calcination is effected at 550° C. for 4 hours in a muffle furnace without an air stream. 12.9 g of the above catalyst are introduced into the reactor, and 5.8 g/h of cyclopentadiene (0.088 mol/h), 2.3 l/h of $NH_3$, 15 l/h of air, 20 g/h of $H_2O$ and 8.0 l/h of $N_2$ are conducted through the reactor at 420° C. The conditions correspond to those of Example 1 (Table 1, item 1a) in German Offenlegungsschrift No. 2,401,103, except that cyclopentadiene is reacted instead of propylene.

Duration of experiment: 4 h.
Yield of pyridine: 0%.

We claim:

1. Process for the preparation of pyridine by ammoxidation at elevated temperature of a $C_5$ hydrocarbon using a catalyst based on $SiO_2$ and/or $Al_2O_3$ with a large surface area and a large pore volume, wherein
   (a) cyclopentadiene is used as the $C_5$ hydrocarbon, and
   (b) silica gel, $\gamma$-$Al_2O_3$ and/or aluminum silicate(s) in tellurium-free form, if appropriate doped with oxides of transition metals and/or of gallium and/or indium, having a surface area of between about 75 and 800 $m^2/g$ and a pore volume of between about 0.2 and 2 $cm^3/g$ are used as the catalyst based on $SiO_2$ and/or $Al_2O_3$ and
   (c) the ammoxidation is carried out at temperatures of from about 200° to 400° C., preferably from about 250° to 350° C.

2. Process as claimed in claim 1, wherein the catalyst is doped with $V_2O_5$.

3. Process as claimed in claims 1 to 2, wherein the catalyst is doped with about 0.5 to 10% by weight of the doping agent.

4. Process as claimed in claims 1 to 3, wherein the catalyst also contains trivial quantities of further customary additives.

* * * * *